United States Patent [19]

MacNeill

[11] 4,346,869
[45] Aug. 31, 1982

[54] TUBE CLAMP

[76] Inventor: Robert L. MacNeill, 54 High St., Newburyport, Mass. 01950

[21] Appl. No.: 242,848

[22] Filed: Mar. 12, 1981

[51] Int. Cl.³ .............................................. F16K 7/04
[52] U.S. Cl. ..................................... 251/10; 128/346
[58] Field of Search .................... 251/9, 10; 24/248 B, 24/255 SL; 128/346

[56] References Cited

U.S. PATENT DOCUMENTS

| 820,216 | 5/1906 | Leffingwell et al. | 251/10 |
| 3,766,925 | 10/1973 | Rubricus | 24/255 SL |
| 3,824,654 | 7/1974 | Takabayashi | 24/255 SL |
| 3,874,042 | 4/1975 | Eddleman et al. | 251/10 |
| 4,038,726 | 8/1977 | Takabayashi | 24/248 R |
| 4,227,730 | 10/1980 | Alexander et al. | 128/346 |

FOREIGN PATENT DOCUMENTS 390670 2/1924 Fed. Rep. of Germany ...... 128/346

Primary Examiner—H. Jay Spiegel
Attorney, Agent, or Firm—Harvey B. Jacobson

[57] ABSTRACT

A pair of elongated jaw members are provided and interconnected at one pair of corresponding ends in generally parallel relation through the utilization of an open loop member having opposite ends formed integrally with the adjacent jaw member ends. The jaw members and the loop member are constructed of stiff but resilient plastic and one of the jaw members includes an integral arm projecting laterally outwardly therefrom across the adjacent end of the other jaw member. The arm includes longitudinally spaced ratchet teeth thereon with which the adjacent end of the other jaw member is selectively engageable and the included angle formed between the one jaw member and the arm is slightly less than 90°, the connection between the arm and the one jaw member end from which it is supported being sufficiently deformable to allow angular displacement of the arm to a position with the included angle formed between the arm and the one jaw member exceeding 90°. One of the jaw members is formed with a partial cylindrical groove extending longitudinally of the side thereof opposing the other jaw member and the other jaw member is provided with a partial cylindrical longitudinal rib of slightly less radius of curvature receivable in the aforementioned groove to clamp a resilient tube section tightly closed between the jaw members.

2 Claims, 5 Drawing Figures

U.S. Patent     Aug. 31, 1982     4,346,869
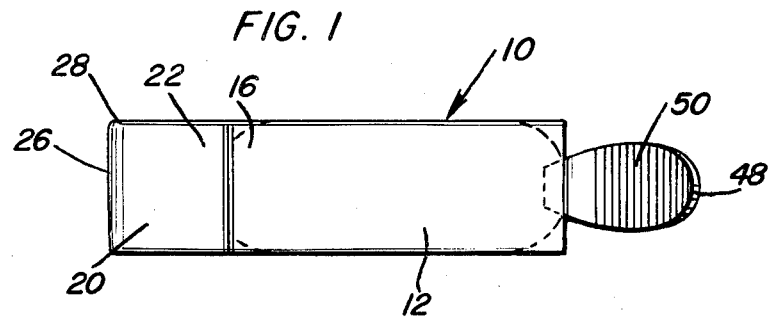
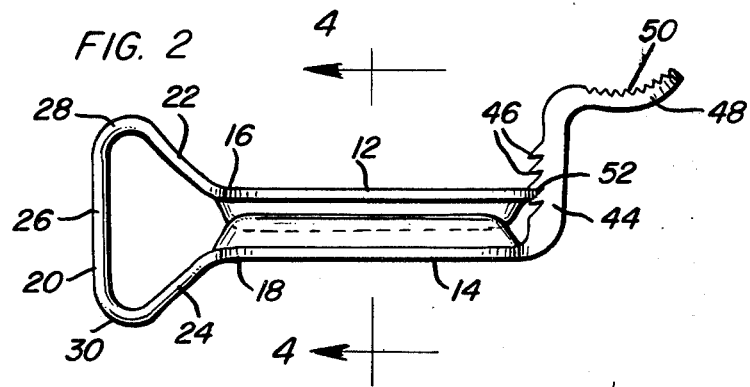
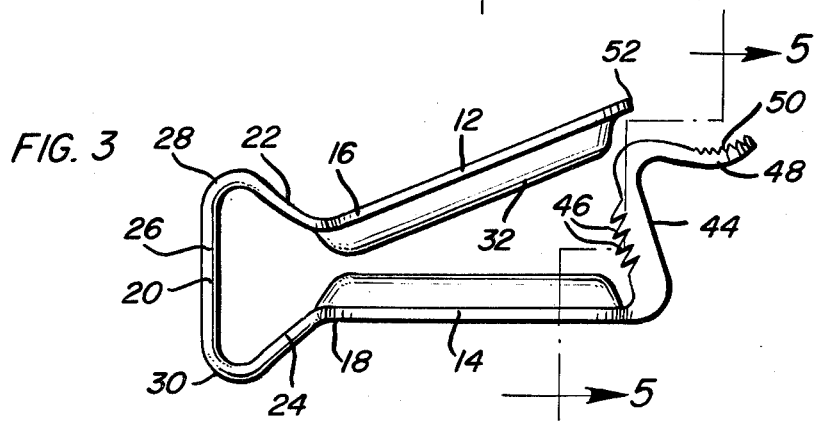
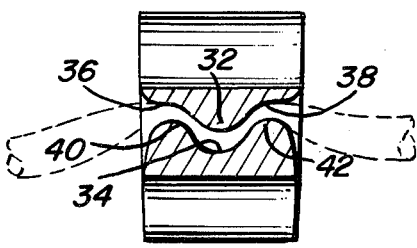
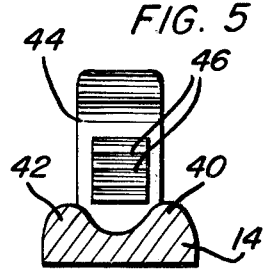

TUBE CLAMP

BACKGROUND OF THE INVENTION

At the present time when carrying out hemodialysis operations, various blood lines and associated plastic tubings are clamped with various surgical clamps made of stainless steel. There are between six and eight clamps used per patient and these clamps must be replaced on a regular bases due to breakage, loss or misappropriation at considerable cost. Accordingly, a need exists for an inexpensive reuseable clamp which will be effective for clamping blood lines and associated plastic tubings in use during hemodialysis operations.

Various forms of reuseable clamps which have been designed for different purposes are disclosed in U.S. Pat. Nos. 3,713,622, 3,766,925, 3,825,012, 3,874,042 and 4,038,726. However, these previously known forms of clamps are either not particularly well adapted for use in conjunction with hemodialysis blood lines and associated plastic tubes, or they are expensive to produce and/or cumbersome to use.

BRIEF DESCRIPTION OF THE INVENTION

The clamp of the instant invention has been specifically designed for manufacture at a low cost and to be effective in variably clamping hemodialysis blood lines and associated plastic tubes. In addition, the clamp is constructed in a manner whereby it may be effectively, adjustably, clampingly engaged with a blood line or an associated plastic tubing by only one hand of the user and is further constructed in a manner whereby the user of the clamp may adjustably increase or decrease the clamping action thereof on an associated blood line or associated plastic tubing.

In addition, the clamp is constructed with opposed clamping surfaces which may be clampingly engaged with a blood line or associated tubings in a manner which will not cause damage to the blood lines and tubing.

The main object of this invention is to provide an inexpensive and reuseable clamp for efficient use during hemodialysis operations.

Another object of this invention is to provide a clamp in accordance with the preceding object and which may be manufactured at a low cost.

Still another object of this invention is to provide a clamp which may be readily clampingly associated with a blood line or associated tubing by only one hand of the user.

A further important object of this invention is to provide a clamp which may be adjustably increased in its clamping action on an associated blood line or tubing and which may also be adjustably decreased in its clamping action while being manipulated, with ease, by only one hand of the user.

Still another object is to provide a clamp which may be used with tubing of different diameters, from one-eighth inch to five-eighth inch in diameter, and which will not slip when engaged with tubing of these different diameters.

A final object of this invention to be specifically enumerated herein is to provide a clamp in accordance with the preceding objects and which will conform to conventional forms of manufacture, be of simple construction and easy to use, so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a top plan view of the clamp;

FIG. 2 is a side elevational view of the clamp with the clamp in a fully closed position;

FIG. 3 is a side elevational view of the clamp in an open position;

FIG. 4 is a transverse vertical sectional view taken substantially upon the plane indicated by the section line 4—4 of FIG. 2; and FIG. 5 is a transverse vertical section view taken substantially upon the plane indicated by the section line 5—5 of FIG. 3.

DETAILED DESCRIPTION OF THE INVENTION

Referring now more specifically to the drawings, the numeral 10 generally designates the clamp of the instant invention. The clamp 10 includes a pair of elongated first and second jaw members 12 and 14 including a first pair of corresponding ends 16 and 18.

The clamp 10 additionally includes an open loop member 20 having opposite ends 22 and 24 formed integrally with the ends 16 and 18 of the jaw members 12 and 14. The clamp 10 is constructed of a stiff but deformable and resilient plastic material and the jaw members 12 and 14 normally assume the relative positions thereof illustrated in FIG. 3 of the drawings.

The open loop member 20 includes a central longitudinally straight bight portion 26 and a pair of longitudinally straight arms defining the ends 22 and 24 integrally connected to opposite ends of the bight portion 26 by curved portions 28 and 30.

The jaw member 12 includes a longitudinally extending partial cylindrical rib 32 opposing the jaw member 14 and the jaw member 14 defines a partial cylindrical groove 34 extending longitudinally thereof opposing the jaw member 12. The radius of curvature of the rib 32 is slightly less than the radius of curvature of the groove 34 and, accordingly, the rib 32 may be received within the groove 34 with the double thickness of the opposite side wall portions of a thin blood line or tube clamped between the rib 32 and the groove 34. The opposite side portions of the rib 32 include reversely curving partial cylindrical surfaces 36 and 38 and the opposite side portions of the groove 34 include reversely curving partial cylindrical surfaces 40 and 42. Accordingly, the clamp 10 is totally devoid of sharp edges or corners which might cause damage to tubes or blood lines with which the clamp 10 is clampingly engaged.

The end of the jaw member 14 remote from the open loop member or frame 20 includes a laterally directed arm or tongue 44 formed integrally with the jaw member 14 and projecting to the side of the jaw member 14 upon which the jaw member 12 is disposed. The side of the tongue or arm 44 opposing the loop member 20 is provided with longitudinally spaced ratchet teeth 46 and the end of the tongue or arm 44 remote from the jaw member 14 is provided with a digit engageable tab 48 provided with a serrated surface as at 50. The tongue or arm 44 is formed integrally with the adjacent end of the jaw member 14 and normally defines an included angle of slightly less than 90° between the tongue 44 and the jaw member 14. However, the material of which the clamp 10 is constructed is sufficiently deformable and resilient to enable thumb or finger pressure to be applied to the tab 48 in order to bias the free end of the tongue or arm 44 away from the open loop or frame member 20 in order to enable the free end edge or lip 52 of the jaw member 12 to be depressed downwardly and engage with the teeth 46 for retaining the jaw member 12 in predetermined spaced relationship relative to the jaw member 14.

It may thus be seen that the clamp 10 may be held in the four fingers of one hand and that the tongue 48 may be engaged by the thumb of the same hand while the clamp 10 is either adjustably clamped on a tube or blood line or released from clamped engagement with a tube or blood line.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A fluid flow blocking pump for use in conjunction with blood lines and associated tubing sections presently used during hemodialysis procedures, said clamp comprising a one-piece construction including first and second elongated, side-by-side and generally parallel longitudinally straight jaw members including first and second pairs of corresponding ends, an open loop member having spaced opposite ends formed integrally with one pair of said corresponding ends, said jaw members and loop member being constructed of shape retentive and slightly resilient plastic material with said loop interconnecting said one pair of jaw member ends for relative angular swinging of said jaw members between closed juxtaposed substantially parallel positions and open positions with said jaw members swung at least slightly away from each other and divergent toward the second pair of corresponding ends thereof, said jaw members, when in said closed positions, including closely juxtaposed parallel sides, one of said juxtaposed sides including a lengthwise extending elongated raised rib thereon of smooth substantially sine wave shape in cross section, the other of said juxtaposed sides defining a lengthwise extending elongated channel of substantially sine wave shape in cross section and with the radius of curvature of the apex portion of the first mentioned sine wave shape being slightly less than the radius of curvature of the second mentioned sine wave shape, one of the other pair of corresponding ends of said jaw members including a transverse terminal end lip and the other end of said other pair of corresponding ends including a generally right angulated elongated tongue formed integrally therewith, said tongue extending outwardly of said other end in the direction in which the other jaw member is swingable toward the open position and including transversely extending longitudinally spaced ratchet teeth formed on the side thereof facing said loop member, said ratchet teeth facing away from the free end of said tongue and engageable by said lip to releasably prevent relative swinging movement of said jaw members toward said open positions, the juncture of said tongue with said other end of said other pair of corresponding ends being somewhat flexive and resilient, whereby said tongue may be swung, slightly away from said loop, to disengage said teeth from said lip, said tongue, in non-flexed condition, being inclined slightly inwardly toward the connecting loop member end of said jaw members, said loop member, when in a relaxed state, including a pair of generally straight arm portions convergent toward one pair of ends thereof comprising said opposite ends of said loop member, and an integral elongated and generally longitudinally straight connecting bight member extending between and connecting the other pair of ends of said arm portions, said jaw members being generally strap-like in configuration and said rib being formed on the side of one of said strap-like jaws opposing the other jaw, said other jaw member including a pair of laterally and longitudinally extending ribs formed thereon on the side opposing said one jaw member and said channel is defined between said pair of ribs.

2. The combination of claim 1 wherein the outer end of said tongue includes a generally right angulated finger or thumb engageable tab supported therefrom directed away from said loop member.

* * * * *